(12) United States Patent
Smith

(10) Patent No.: US 6,461,301 B2
(45) Date of Patent: Oct. 8, 2002

(54) RESONANCE BASED PRESSURE TRANSDUCER SYSTEM

(75) Inventor: Leif Smith, Uppsala (SE)

(73) Assignee: Radi Medical Systems AB, Uppsala (SE)

(*) Notice: Subject to any disclaimer, the term of this patent is extended or adjusted under 35 U.S.C. 154(b) by 12 days.

(21) Appl. No.: 09/810,415

(22) Filed: Mar. 19, 2001

(65) Prior Publication Data

US 2001/0037066 A1 Nov. 1, 2001

Related U.S. Application Data

(60) Provisional application No. 60/199,349, filed on Apr. 25, 2000.

(30) Foreign Application Priority Data

Mar. 21, 2000 (EP) ............................................ 00850051

(51) Int. Cl.[7] .................................................. A61B 8/00
(52) U.S. Cl. ...................... 600/438; 600/459; 600/437; 600/480; 73/704; 73/715
(58) Field of Search ................................ 600/437–472; 73/704, 715

(56) References Cited

U.S. PATENT DOCUMENTS

| | | | |
|---|---|---|---|
| 5,142,912 A | 9/1992 | Frische | 73/702 |
| 5,226,423 A | 7/1993 | Tenerz et al. | 128/673 |
| 5,619,997 A | 4/1997 | Kaplan | 128/660.02 |
| 6,182,513 B1 * | 2/2001 | Stemme et al. | 73/704 |
| 6,312,380 B1 * | 11/2001 | Hoek et cl. | 600/437 |

\* cited by examiner

*Primary Examiner*—Marvin M. Lateef
*Assistant Examiner*—Ruby Jain
(74) *Attorney, Agent, or Firm*—Foley & Lardner

(57) ABSTRACT

The invention relates to a resonance based pressure transducer system, insertable into a living body for the in vivo measurement of pressure. It comprises a pressure sensor (2) having a mechanical resonator (16), the resonance frequency of which is pressure dependent; and a source of ultrasonic energy (4). The sensor (2) is mechanically coupled to said source (4) of ultrasonic energy, and the sensor and the source of ultrasonic energy are provided on a common, elongated member (6) at the distal end thereof. A system for pressure measurement comprises an AC power supply, a resonance based pressure transducer system, and a control unit for controlling the supply mode of the AC power, and for analyzing a resonance signal emitted from the resonance based pressure transducer system.

15 Claims, 6 Drawing Sheets

RESONANCE BASED PRESSURE TRANSDUCER SYSTEM

This application claims the benefit of priority of European application 00850051.4, filed Mar. 21, 2000, and U.S. provisional application No. 60/199,349, filed Apr. 25, 2000. The entire contents of both of these applications are incorporated herein by reference. The present invention relates generally to devices for measuring physiological pressures, and in particular to such devices and systems employing resonance as the vehicle for information transmission.

BACKGROUND OF THE INVENTION

The need for measuring and recording physiological pressures, for example, in the coronary vessels, has triggered the development of miniaturized devices for enabling the access to the very narrow vessels, such as coronary vessels. Typically a sensor of very small size is mounted on a guide wire, which is inserted in e.g. the femoral artery and guided to the desired point of measurement, e.g. a coronary vessel. There are certain problems associated with the integration of a pressure sensor onto a guide wire suitable for the type of measurements mentioned above. The first and foremost problem is to make the sensor sufficiently small. Also, the number of electrical connections and leads should be minimized, in order to obtain a sufficiently flexible guide wire which can be guided to the desired location through the coronary vessels without too much difficulty. One way of eliminating the electrical leads and connections is to employ a resonance sensor which reacts on external stimuli in the form of e.g. ultrasonic energy by emitting a resonance frequency that can be correlated to pressure prevailing in the environment where the sensor is located. Such a device is disclosed in our co-pending U.S. patent application, Ser. No. 09/219,798, filed Dec. 23, 1998, and whose entire contents are incorporated herein by reference.

Another example is disclosed in U.S. Pat. No. 5,619,997 (Kaplan). It relates to a passive sensor system using ultrasonic energy, and comprises an implantable sensor capable of responding to ultrasound by emitting a resonance that is detectable and which varies in accordance with the variations of a selected physical variable.

A drawback with these systems is that they require an external source of ultrasonic energy, which is located outside the body in the vicinity of the measurement location. It makes the systems bulky and it may be difficult to accurately know the position of the resonance sensor inside the body, and thus the quality of the signal can be less than optimal.

SUMMARY OF THE INVENTION

Therefore, the object of the present invention is to provide a system that overcomes the drawbacks indicated above.

This object is achieved with a resonance pressure transducer system as described below. Thereby, a resonance sensor is arranged in close proximity to, preferably mounted on, a source of ultrasonic energy, e.g. a piezo-electric crystal capable of generating oscillations in the frequency range 10 kHz to 100 MHz.

Preferably the system is provided on a wire, e.g. a guide wire, to facilitate insertion into the body of a patient.

In a further aspect of the invention there is provided a pressure measurement system, comprising an AC power supply; a resonance based pressure transducer system; and a control unit for controlling the supply mode of the AC power, and for analyzing a resonance signal emitted from the resonance based pressure transducer system.

BRIEF DESCRIPTION OF THE DRAWINGS

The invention will now be described in detail with reference to the drawings, in which.

DETAILED DESCRIPTION OF THE INVENTION

For the purpose of this application the expression "mechanical coupling" or "mechanically coupled" shall be taken to encompass any connection between two elements that permits the transfer of vibrations, particularly in the ultrasonic range, from one element to another.

Figure 1:
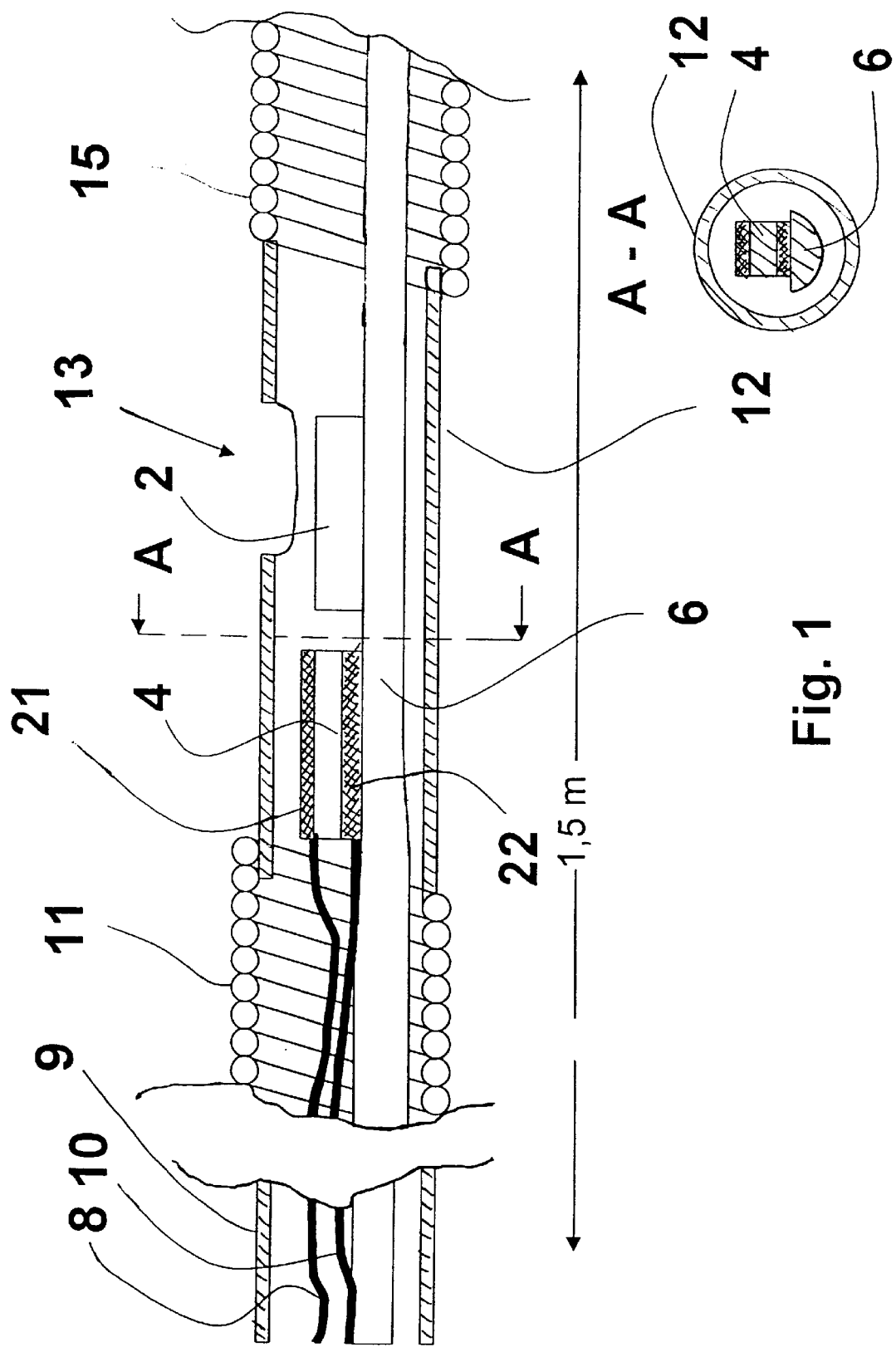
FIG. 1 illustrates a first embodiment of a system according to the invention.

FIG. 1 illustrates schematically the inventive idea, namely the provision of a resonance sensor 2 responding to ultrasonic energy by resonating at a selected frequency, the resonating frequency of which being subject to a frequency shift when the sensor is exposed to a pressure differential. It also comprises a source 4 of ultrasonic energy located in close proximity to said sensor. The amount of energy stored by the resonator is very small. Therefore it is essential that the distance between the source and the resonator is very small, in order to enable a reasonable detection level. The longer the spacing between the two is, the more difficult it will be to detect the resonance. In the shown embodiment the sensor and energy source are both attached to the distal end portion of a core wire 6 running inside a guide wire, suitably of the order of 1.5 m in length, in order to enable that they be easily inserted into the body of a patient, and manipulated to a measurement site. The guide wire comprises a proximal tube 9, a coil 11 for providing flexibility, and at the distal end portion it comprises the sensor assembly 2, 4, mounted on the core wire 6. The sensor is preferably enclosed in a protective tube segment 12 with an aperture 13, such that the surrounding medium will have access to the resonance sensor 2. Attached to the distal end of the tube segment 12 is a second coil 15. The ultrasonic source is electrically energized by the supply of a high-frequency AC voltage, e.g. at 10 kHz–100 MHz and 1–100 V. The electrical energy is supplied via electrical leads 8, 10. The core wire 6 could be used as one lead if desired, in order to bring down the number of leads to one.

The source of ultrasonic energy preferably consists of a plate of piezoelectric material, e.g. lead zirconate titanate (PZT), adhesively bonded to a flat surface of the guide wire 6. The plate 4 will include electrodes 21, 22 attached to at least two of its surfaces and connected to the leads 8 and 10. Upon application of an AC voltage between these electrodes, mechanical vibrations synchronous with the applied AC frequency will be generated in the plate 4. These vibrations will propagate via the guide wire 6 to the resonance sensor 2.

The wire 6 may consist of the core wire of a guide wire assembly as stated above, but may also be any elongated member, housing the resonance sensor 2 and the PZT element 4. For example, it may consist of a thin wire functioning as an antenna for wireless communication between the PZT element 4 and an external electronic unit.

Figure 2:
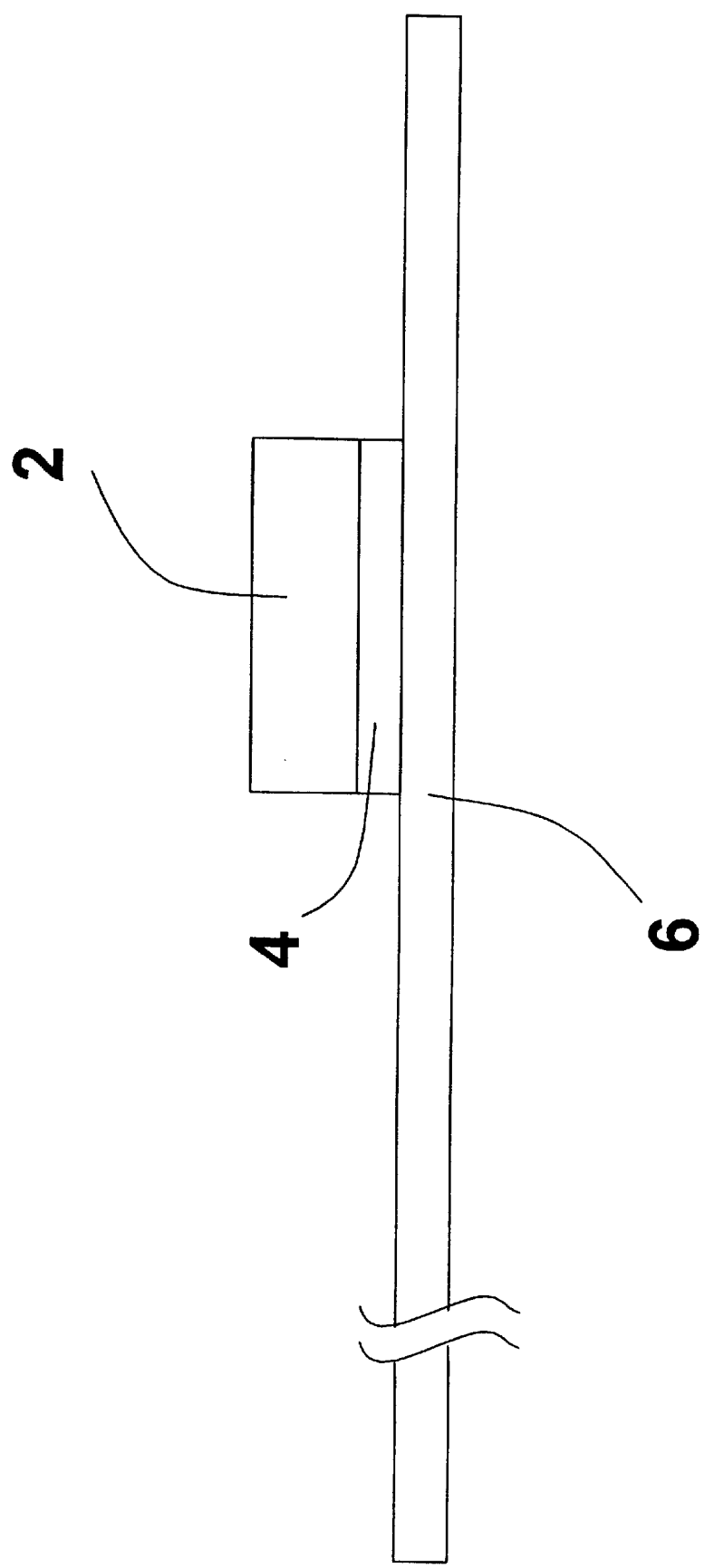
FIG. 2 illustrates a second embodiment of a system according to the invention.

In FIG. 2 another embodiment is shown, for simplicity without electrical leads and protective tube. Here the resonance sensor 2 is attached on top of the piezo-oscillator 4. In this way there is an intimate contact between the source of ultrasonic energy and the resonating structure, whereby a very efficient energy transfer is obtained.

Figure 3:
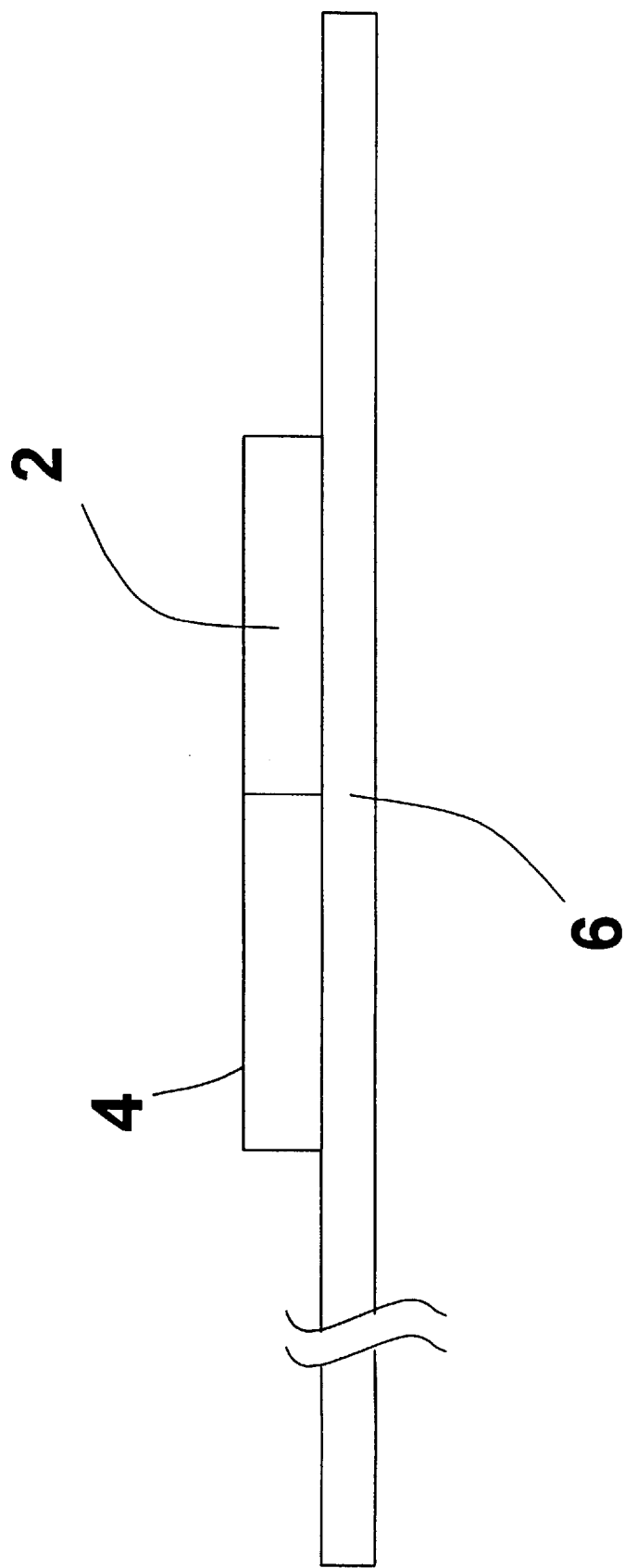
FIG. 3 illustrates a third embodiment of a system according to the invention.

A third variant is also conceivable, where the sensor 2 and the energy source 4 are connected end-to-end to each other, as shown in FIG. 3.

Figure 4:
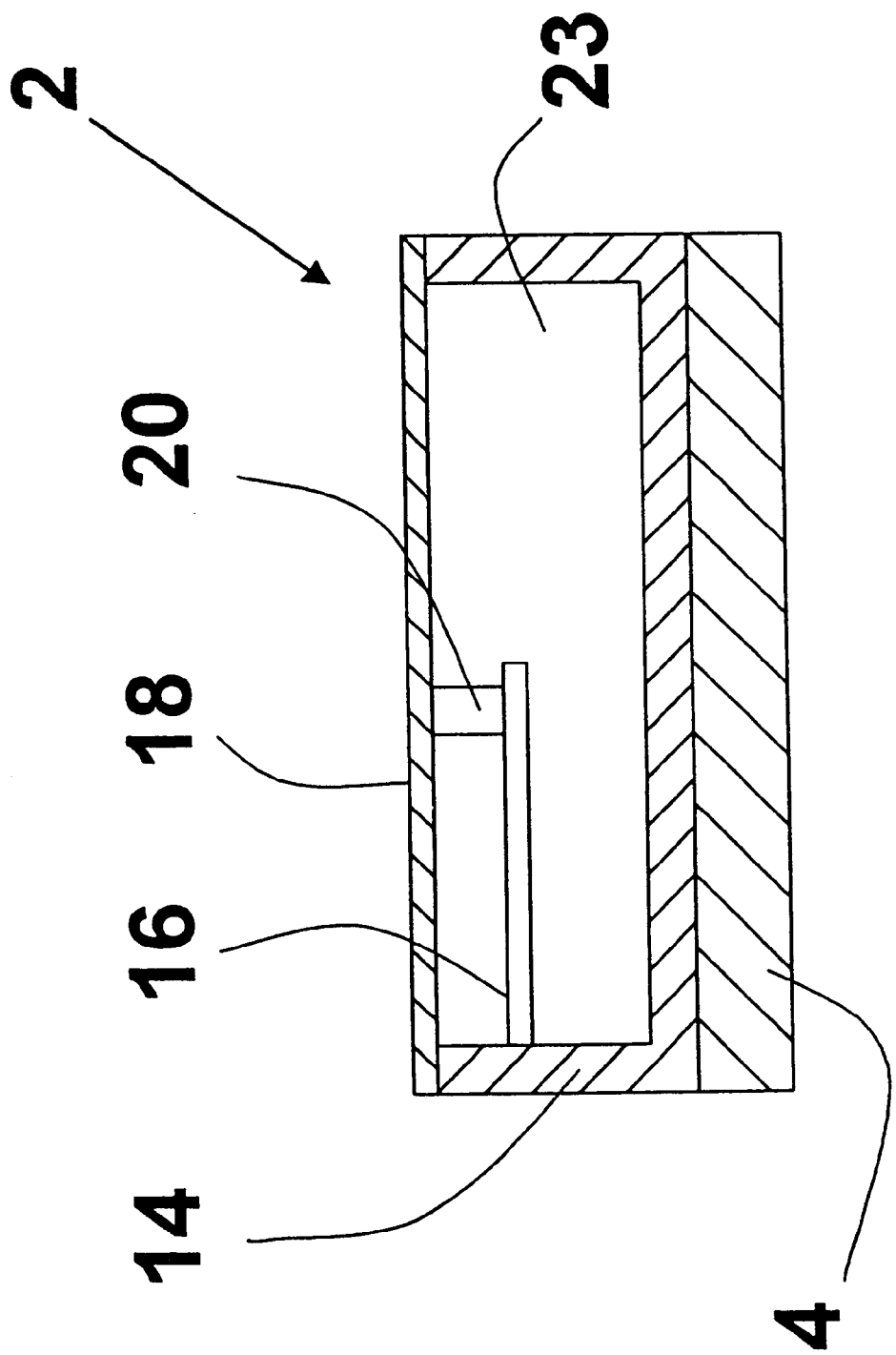
FIG. 4 illustrates a preferred embodiment of a sensor/energy source assembly according to the invention.

The preferred embodiment is the one shown in FIG. 2. A preferred structure of sensor/energy source assembly is illustrated in some detail, although schematically, in FIG. 4.

Thus, a piezo-electric element (or crystal) 4 is provided, on a surface of which a resonance unit 2 is mounted in intimate contact therewith. The resonance unit is attached by means of a non-damping mechanical coupling, i.e. the energy emitted by the piezo-electric element must not be absorbed in the connection area to any significant extent. There are several possible ways of attaching, such as by bonding in general terms, gluing or soldering, just to mention some. The resonance unit comprises a cell 14, having a bottom and side walls, forming a box-like structure. The open end of the box 14 is closed by a thin membrane 18. Inside the cell there is a resonant beam structure 16, that can have various different shapes, such as a thin membrane like shape, the geometry of which also can be varied. The beam 16 is attached at one end to a cell wall, and the other end is attached to a suspension element 20, which is attached to the membrane 18. The beam 16 has a unique resonance frequency, the value of which varies in dependence of the strain in the material constituting the beam. In response to a pressure change in the environment surrounding the sensor 2, which causes a change in pressure differential across the membrane 18, the membrane will either deflect inwards or outwards, and thereby cause the beam 16 also to deflect accordingly, since it is connected to the membrane via the suspension element 20. A suitable sensor of this type is disclosed and claimed in U.S. patent application Ser. No. 09/219,794 (now U.S. Pat. No. 6,182,513) with the same assignee as the present application. The entire contents of this US Patent are incorporated herein by reference.

The chamber or cavity 23 housing the beam 16 is preferably evacuated in order to minimize viscous damping of the resonant vibrations of the resonance unit 2. The quality factor Q of the resonance, defined as the ratio between the reactive and dissipative energy of the vibrations, should be as high as possible in order to provide adequate measurement accuracy. An optimized design and construction of the resonance sensor 2, using silicon micro-machining techniques, will typically yield a Q value of 10 or more, preferably 50 or more, most preferably 100 or more.

In a preferred embodiment the ultra sound source is a unit made of PZT, which commonly is amorphous, or polycrystalline. The source is used for both "excitation" and "listening", i.e. it transmits energy to cause resonance in the resonator, and it also receives energy of the resonance frequency from the resonating beam in the sensor via the "box" structure, thereby generating an output signal that is detected.

This requires that the crystal be operated at a frequency that matches the resonance frequency of the resonator.

There are several possible modes of operation of a device according to the invention (in this regard reference can be had to our unpublished International Application PCT/SE99/02467, incorporated by reference).

Figure 5B:
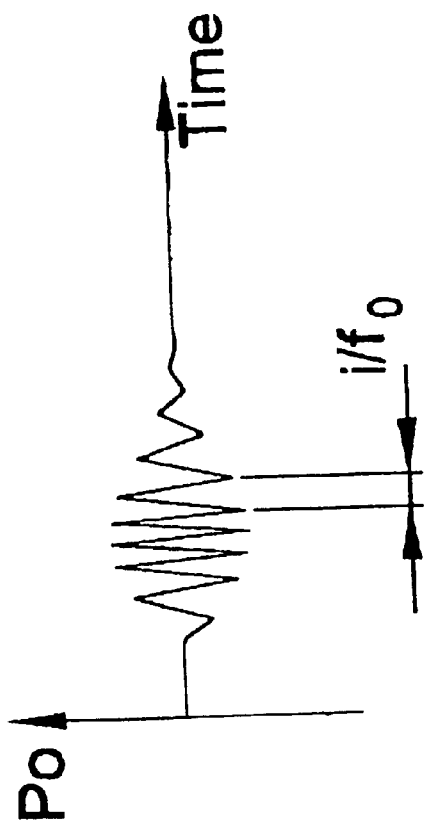
FIGS. 5a and 5b show typical waveforms for excitation and detection.
Figure 5A:
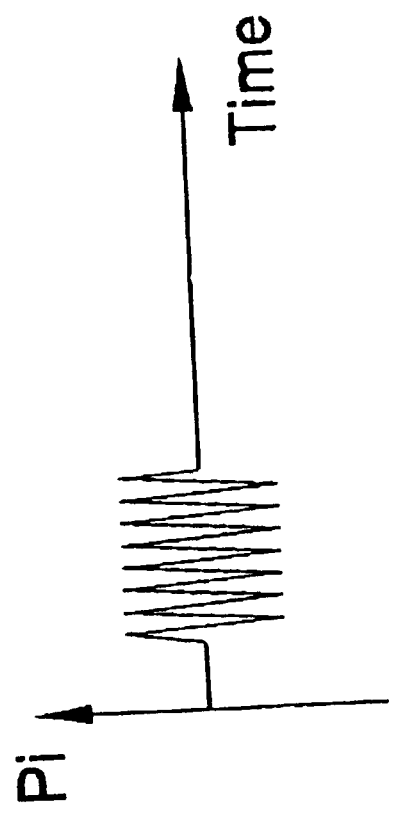

Typical waveforms for excitation and detection are shown in FIGS. 5a and 5b, respectively. The excitation waveform is a burst of sine waves. In an acoustic/mechanical system, a preferable excitation frequency is 1 MHz, and the burst consists of 10–1000 periods, depending on the quality factor Q of the resonator. A larger number of periods is more desired when the quality factor Q is high, because a larger oscillation amplitude is induced. FIG. 5b depicts such a build-up of the oscillations. When the external power source causing excitation is switched off, power will be emitted from the resonator and decays at a rate also determined by the quality factor Q. The frequency of the free oscillations $f_o$ is equal to the resonance frequency of the resonator.

The burst of sine waves according to FIG. 5 is followed by a relaxation period until the next burst. The relaxation periods are preferably longer than the duration of the bursts.

A first preferred mode is thus to excite the PZT unit with short pulses of applied voltage. Such excitation comprises a very broad spectrum of excitation frequencies (ideally a short pulse, with a duration not exceeding the period of time corresponding to the resonance frequency of the resonance sensor 2). Thus, there will always be some energy available in the pulse, which will cause the resonator to vibrate at its resonance frequency.

Between pulses, there will be periods of no excitation. During this time period the resonator will yield a decaying oscillation at its resonance frequency. The PZT unit will be affected by the resonance energy from the resonator, and a voltage will be generated in the unit. The change in voltage response caused by the vibrating crystal when exposed to a pressure differential compared to the response at nominal pressure is measured, and can be converted into a pressure value.

The actual nominal resonance frequency of the resonance sensor at standard conditions (e.g. 25° C. and 1 bar pressure) is determined during manufacturing.

Alternatively, continuous sine wave excitation can be used. If the sine wave excitation is swept continuously in a frequency range encompassing the resonance frequency of the sensor 2, then the resonance will manifest itself as a sharp peak of the mechanical load of the PZT element 4. In turn, this will influence the electrical impedance of the PZT element which may be measured remotely by the connecting leads 8, 10.

Figure 6:
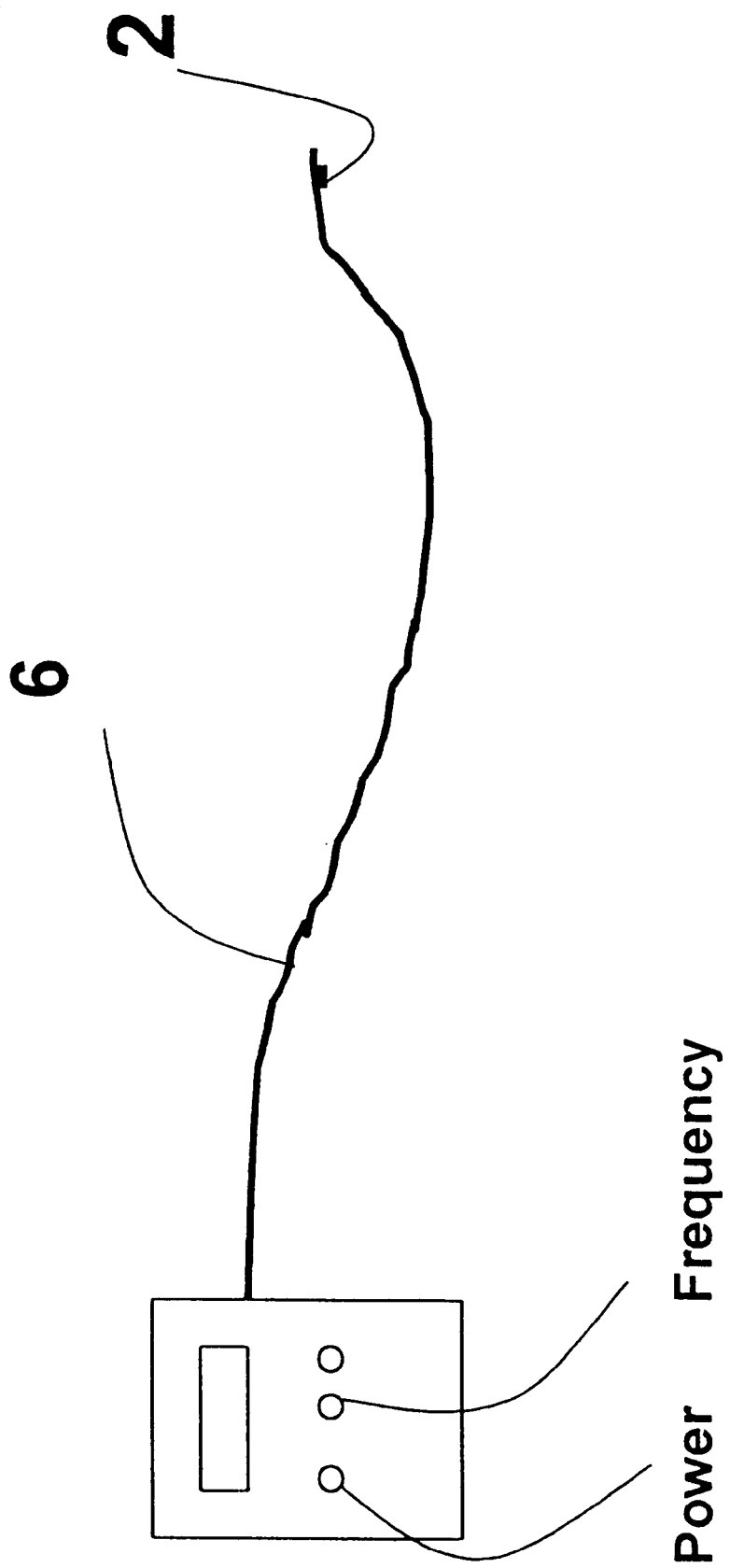
FIG. 6 is a schematic illustration of a system comprising the invention.

A complete system for pressure measurements, schematically illustrated in FIG. 6, will include an AC power source capable of delivering output voltages in a controlled manner. This control is provided by a suitable control unit such as a computer, programmed for a number of excitation options. Thus, the excitation mode can be selected to suit the particular measurement at hand.

The actual procedure is performed as follows.

The piezo-electric device is energized with an AC voltage at a suitable frequency in the range 10 kHz to 100 MHz. It generates an ultrasonic wave hitting the resonator (beam) inside the sensor box structure which begins to vibrate at its resonance frequency. If the membrane in the sensor structure is subjected to a pressure different from ambient, it will be deflected, thereby causing the resonator to experience some strain, which will change the resonance frequency. The excitation voltage is switched off, and the piezo-electric element will be exposed to the decaying resonance output from the resonator, thereby producing a piezo-electric voltage of the same frequency as the vibrating resonator, that is detectable, and that can be correlated to the pressure differential.

The piezo-electric element must be capable of detecting the entire dynamic frequency range that the resonating beam in the sensor generates due to pressure changes, e.g. 1 atm+/−500 mm Hg.

What is claimed is:

1. A resonance based pressure transducer system, insertable into a living body for in vivo measurement of pressure, comprising a pressure sensor (2) having a mechanical resonator (16), a resonance frequency of which is pressure dependent; and a source of ultrasonic energy (4);

wherein the sensor (2) is mechanically coupled to said source (4) of ultrasonic energy, and wherein the sensor and the source of ultrasonic energy are provided on a common, elongated member (6) at a distal end thereof.

2. The resonance pressure transducer system as claimed in claim 1, wherein the sensor (2) is mounted on said source (4) of ultrasonic energy.

3. The resonance pressure transducer system as claimed in claim 1, wherein the common, elongated member is a wire (6).

4. The resonance pressure transducer system as claimed in claim 3, wherein said source of ultrasonic energy (4) is attached to said wire (6).

5. The resonance pressure transducer system as claimed in claim 1, wherein the sensor (2) and said source of ultrasonic energy (4) are both attached to a wire (6), and mounted adjacent to each other.

6. The resonance pressure transducer system as claimed in claim 1, wherein said source of ultrasonic energy (4) is a piezo-electric element, capable of generating oscillations of a frequency in a range of 10 kHz to 100 MHz.

7. The resonance pressure transducer system as claimed in claim 6, further comprising electrical connections (10) for enabling applying a voltage to said piezo-electric element.

8. The resonance pressure transducer system as claimed in claim 1, wherein said sensor (2) comprises a membrane (18), a beam (16) attached to said membrane (18) by a suspension element (20), said beam (16) being housed within an evacuated chamber (23).

9. The resonance pressure transducer system as claimed in claim 1, wherein the resonance frequency of said sensor (2) has a quality factor (Q) exceeding 10.

10. The resonance pressure transducer system as claimed in claim 1, wherein excitation of said source (4) of ultrasonic energy uses pulses having a duration not exceeding the period time corresponding to the resonance frequency of the sensor (2).

11. The resonance pressure transducer system as claimed in claim 1, wherein excitation of said source (4) of ultrasonic energy uses sine waves, swept in a frequency range encompassing the resonance frequency of the sensor (2).

12. The resonance pressure transducer system as claimed in claim 1, wherein said sensor (2) comprises a cell (14), having a bottom and side walls, forming a box-like structure.

13. The resonance pressure transducer system as claimed in claim 12, wherein an open end of the cell (14) is closed by a thin membrane (18) thus forming a vacuum cavity, in which a mechanical resonator (16) is provided.

14. The resonance pressure transducer system as claimed in claim 8, wherein the beam (16) has a unique resonance frequency, a magnitude of which is variable in dependence of a strain in a material from which the beam is made.

15. A pressure measurement system, comprising an AC power supply capable of delivering AC power in the frequency range of 10 kHz to 100 MHz;

a resonance based pressure transducer system as claimed in claim 1; and a control unit for controlling a supply mode of said AC power, and for analyzing a resonance signal emitted from said resonance based pressure transducer system.

* * * * *